United States Patent
Na et al.

(10) Patent No.: US 11,341,662 B2
(45) Date of Patent: *May 24, 2022

(54) MEDICAL PROCEDURE USING AUGMENTED REALITY

(71) Applicant: SKIA, Seoul (KR)

(72) Inventors: Seungwon Na, Yongin-si (KR); Wonki Eun, Gwangmyeong-si (KR); Jun Woo Lee, Seoul (KR); Hyuk Kwon, Seoul (KR); Jong Myoung Lee, Seoul (KR)

(73) Assignee: SKIA, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/222,189

(22) Filed: Apr. 5, 2021

(65) Prior Publication Data

US 2021/0225014 A1 Jul. 22, 2021

Related U.S. Application Data

(63) Continuation of application No. 17/067,509, filed on Oct. 9, 2020, now Pat. No. 10,970,862, which is a
(Continued)

(30) Foreign Application Priority Data

Oct. 30, 2019 (KR) .................... 10-2019-0136031

(51) Int. Cl.
*G06T 19/00* (2011.01)
*G06T 7/33* (2017.01)
(Continued)

(52) U.S. Cl.
CPC .............. *G06T 7/344* (2017.01); *A61B 34/10* (2016.02); *A61B 46/20* (2016.02); *A61B 90/37* (2016.02);
(Continued)

(58) Field of Classification Search
None
See application file for complete search history.

(56) References Cited

U.S. PATENT DOCUMENTS

| 9,498,132 B2 | 11/2016 | Maier-Hein et al. |
| 10,603,118 B2 | 3/2020 | Srimohanarajah et al. |
| 2007/0167701 A1 | 7/2007 | Sherman |
| 2016/0004917 A1 | 1/2016 | Yoshida |

(Continued)

FOREIGN PATENT DOCUMENTS

| CN | 108784832 A | 11/2018 |
| CN | 110123453 A | 8/2019 |

(Continued)

OTHER PUBLICATIONS

Wen et al., "Augmented Reality Guidance with Multimodality Imaging Data and Depth-Perceived Interaction for Robot-Assisted Surgery", Robotics, vol. 6, No. 13—18 pages (May 24, 2017).
(Continued)

*Primary Examiner* — Robert J Craddock
(74) *Attorney, Agent, or Firm* — K&L Gates LLP

(57) ABSTRACT

The present disclosure provides a method of medical procedure using augmented reality for superimposing a patient's medical images (e.g., CT or MRI) over a real-time camera view of the patient. Prior to the medical procedure, the patient's medical images are processed to generate a 3D model that represents a skin contour of the patient's body. The 3D model is further processed to generate a skin marker that comprises only selected portions of the 3D model. At the time of the medical procedure, 3D images of the patient's body are captured using a camera, which are then registered with the skin marker. Then, the patient's medical images can be superimposed over the real-time camera view that is presented to the person performing the medical procedure.

20 Claims, 9 Drawing Sheets

Related U.S. Application Data continuation of application No. 16/863,498, filed on Apr. 30, 2020, now Pat. No. 10,803,608.

(51) Int. Cl.
| | |
|---|---|
| *G06T 7/00* | (2017.01) |
| *G06T 7/174* | (2017.01) |
| *A61B 34/10* | (2016.01) |
| *A61B 90/00* | (2016.01) |
| *A61B 46/20* | (2016.01) |
| *G06T 15/08* | (2011.01) |

(52) U.S. Cl.
CPC ............ *G06T 7/0012* (2013.01); *G06T 7/174* (2017.01); *G06T 15/08* (2013.01); *G06T 19/006* (2013.01); *A61B 2034/105* (2016.02); *A61B 2090/363* (2016.02); *A61B 2090/365* (2016.02); *A61B 2090/367* (2016.02); *A61B 2090/374* (2016.02); *A61B 2090/3762* (2016.02); *G06T 2207/30088* (2013.01); *G06T 2207/30204* (2013.01)

(56) References Cited

U.S. PATENT DOCUMENTS

| | | | |
|---|---|---|---|
| 2017/0161945 | A1 | 6/2017 | Robert et al. |
| 2018/0114325 | A1 | 4/2018 | Sanders et al. |

FOREIGN PATENT DOCUMENTS

| | | |
|---|---|---|
| WO | WO 2005088539 A2 | 9/2005 |
| WO | WO 2019215550 A1 | 11/2019 |

OTHER PUBLICATIONS

Trevisan et al., "Towards Markerless Augmented Medical Visualization", MICCAI International Workshop on Augmented Environments for Medical Imaging and Computer-aided Surgery—10 pages (2004).

Suenaga et al., "Vision-based markerless registration using stereo vision and an augmented reality surgical navigation system: a pilot study", BMC Medical Imaging, vol. 15, No. 51—11 pages (2015).

Macedo et al., "High-Quality On-Patient Medical Data Visualization in a Markerless Augmented Reality Environment", SBC Journal on Interactive Systems, vol. 5, No. 3—12 pages (2014).

"Augmented Reality iPad App Guides Surgeons During Tumor Removal", Medgadget, downloaded from <https://www.medgadget.com/2013/08/augmented-reality-ipad-app-guides-surgeons-during-tumor-removal.html>—3 pages (Aug. 21, 2013).

"VSI Head & Neck—Intraoperative Support for ENT Operations", downloaded from <https://vsi.health/en/holomedicine/head-and-neck/>—9 pages (Mar. 13, 2020).

Beyer et al.: High-Quality Multimodal Volume Rendering for Preoperative Planning of Neurosurgical Interventions, Nov. 2007, 1696-1703 (Year: 2007).

Campana et al.: 3D documentation and visualization of external injury findings by integration of simple photography in CT/MRI data sets (IprojeCT), May 2016, 787-797 (Year: 2016).

Rezk-Salama et al, Opacity Peeling for Direct Volume Rendering, Dec. 7, 2006, EUROGRAPHICS, vol. 25 (2006), No. 3, 597-606 (Year: 2006).

Lee et al.: Medical augment reality using a markerless registration framework , Apr. 2012, 5286-5294 (Year: 2012).

Bartlett: The Use of Augmented Reality in the Operating Room: a Review, Dec. 2009, pp. 1-18 (Year: 2009).

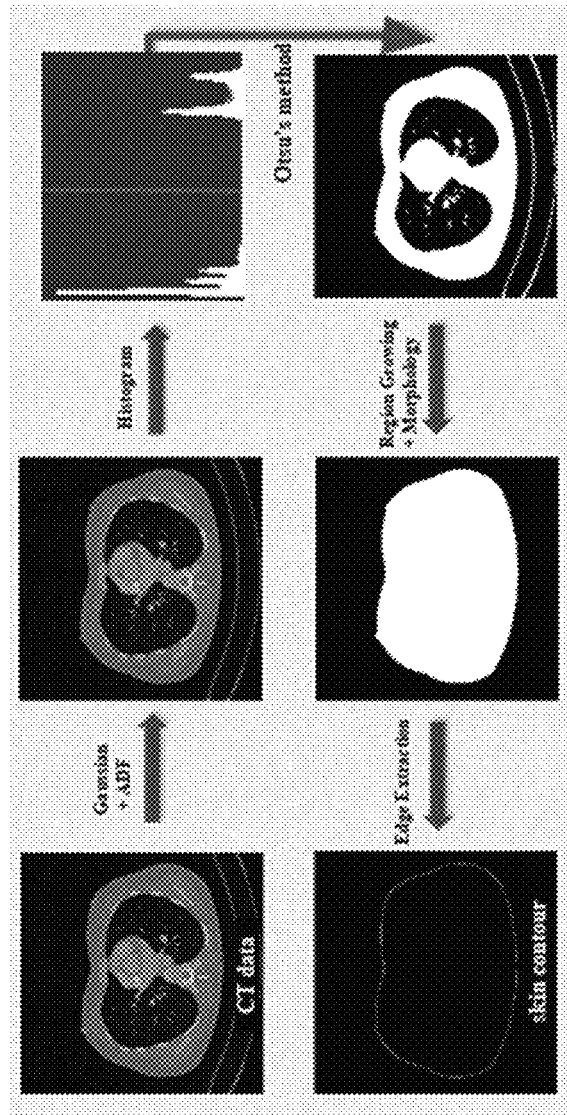
FIG. 1B
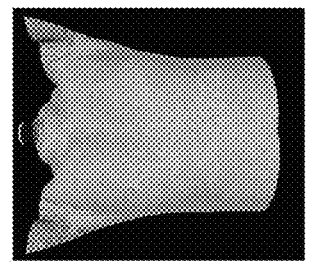
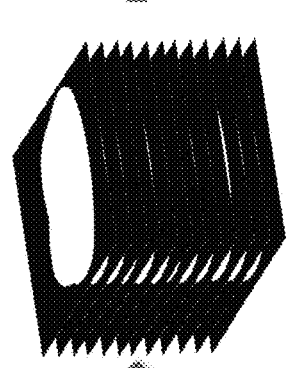
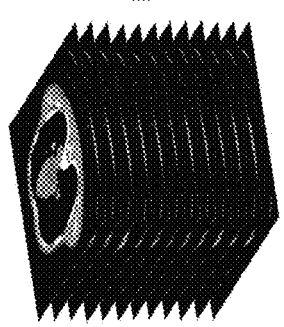
FIG. 1C

MEDICAL PROCEDURE USING AUGMENTED REALITY

CROSS-REFERENCE TO RELATED APPLICATIONS

This application claims the benefit of U.S. patent application Ser. No. 16/863,498 filed Apr. 30, 2020 and U.S. patent application Ser. No. 17/067,509 filed Oct. 9, 2020, and the benefit of Korean Patent Application No. 10-2019-0136031 filed Oct. 30, 2019, the disclosures of which are incorporated herein by reference in their entirety.

BACKGROUND

A high level of interest exists in the medical industry for improving the technologies of visualizing the inside of a patient during a medical procedure. Today, various imaging technologies such as computed tomography (CT) scans and magnetic resonance imaging (MRI) are available to allow a physician to visualize the organs, bones, and other tissues inside the patient's body.

SUMMARY

The present disclosure provides a method of medical procedure using augmented reality for superimposing a patient's medical images (e.g., CT or MRI) over a real-time camera view of the patient. Prior to the medical procedure, the patient's medical images are processed to generate a 3D model that represents a skin contour of the patient's body. The 3D model is further processed to generate a skin marker that comprises only selected portions of the 3D model. At the time of the medical procedure, photos or videos (also referred to herein, individually or collectively, as "images") of the patient's body are captured using a camera, and the camera-captured images are then registered with the skin marker. Because the skin marker is already aligned with the patient's medical images, registering the camera-captured images with the skin marker will also align the patient's medical images with the real-time camera view presented on a display device. Then, the patient's medical images can be superimposed over the real-time camera view.

According to an aspect of the present disclosure, a method for a medical procedure comprises: prior to the medical procedure for treating or examining a target tissue of a patient, processing medical image data comprising a plurality of 2D cross-sectional images of the patient's body encompassing the target tissue to generate a skin 3D model defining a 3D contour of the patient's skin; still prior to the medical procedure, processing the skin 3D model to generate a skin marker, wherein the processing of the skin 3D model comprises removing one or both of (1) a portion of the skin 3D model corresponding to a skin area of the patient that would contact or directly face a supporting surface on which the patient would lie during the medical procedure, and (2) a portion of the skin 3D model corresponding to a skin area of the patient adjacent to a joint of the patient's body that would substantially change its position relative to the target tissue and/or substantially change its contour as a body part of the patient moves about the joint, wherein said removing provides the skin marker; at the time of or during the medical procedure, capturing, using a handheld computing device, images of the patient lying on a patient bed; still at the time of or during the medical procedure, processing the captured images of the patient and the skin marker to register them for augmented reality without use of an artificial physical marker fixed to or placed on the patient's body; and still at the time of or during the medical procedure, rendering, on a display screen of the handheld computing device, a real-time augmented reality view comprising at least one of the plurality of 2D cross-sectional images of the patient's body superimposed on one or more additional real-time images of the patient captured subsequent to the registration.

According to another aspect, the processing of the skin 3D model comprises removing both of (1) a portion of the skin 3D model corresponding to a skin area of the patient that would contact or directly face a supporting surface on which the patient would lie for the medical procedure, and (2) a portion of the skin 3D model corresponding to a skin area of the patient adjacent to a joint of the patient's body that would substantially change its position relative to the target tissue and/or substantially change its contour as a body part of the patient moves about the joint.

According to another aspect, the patient's body comprises a target body part encompassing the target tissue and a non-target body part that is connected to the target body part via a joint, wherein the skin 3D model defines a 3D contour of the patient's skin of the target body part and a 3D contour of the patient's skin of the non-target body part, wherein the processing of the skin 3D model comprises further removing the 3D contour of the patient's skin of the non-target body part.

According to another aspect, the patient's body comprises a target body part encompassing the target tissue and a non-target body part that is connected to the target body part via a joint, wherein the skin 3D model defines a 3D contour of the patient's skin of the target body part and does not define a 3D contour of the patient's skin of the non-target body part.

According to another aspect, the patient's body comprises a target body part encompassing the target tissue and a non-target body part that is connected to the target body part via a joint, wherein the skin 3D model defines a 3D contour of the patient's skin of the target body part and a 3D contour of the patient's skin of the non-target body part, wherein the processing of the skin 3D model comprises further removing the 3D contour of the patient's skin of the non-target body part.

According to another aspect, the medical procedure comprises an open surgery, wherein, in the real-time augmented reality view, at least one of the plurality of 2D cross-sectional images of the patient's body that shows the target tissue is displayed on the display screen over the one or more additional real-time images of the patient for a surgeon to determine an incision location on the patient's body.

According to another aspect, the method further comprises, prior to the medical procedure, processing the medical image data to generate a tissue 3D model defining a 3D contour enclosing the target tissue, wherein the tissue 3D model is located inside the skin 3D model, wherein the real-time augmented reality view further comprises the tissue 3D model superimposed on one or more additional captured images of the patient.

According to another aspect, the processing of the skin 3D model comprises further removing a portion of the skin 3D model corresponding to the patient's skin area that would be covered with a medical drape and therefore would not be exposed during the medical procedure.

According to another aspect, the processing of the skin 3D model comprises further removing a portion of the skin 3D model corresponding to the patient's skin area that would substantially change its contour before and after the patient's meal.

According to another aspect, the skin marker comprises at least two portions corresponding to the patient's skin areas that are not neighboring each other.

According to another aspect, the method further comprises placing a medical drape over the patient lying on the patient bed in a manner that leaves a skin portion of the patient's body exposed, wherein the placing of the medical drape is performed before or after capturing the images of the patient.

According to another aspect, the method further comprises placing a medical drape over the patient lying on the patient bed while leaving a skin area exposed, wherein the placing of the medical drape is performed after the capturing of the images of the patient, wherein the skin marker does not comprise a portion of the skin 3D model corresponding to the skin area that is left exposed.

According to another aspect, the skin marker does not comprise a portion of the skin 3D model corresponding to the patient's skin area that is closest to the target tissue.

According to another aspect, the processing of the skin 3D model comprises further removing at least one portion of the skin 3D model corresponding to at least one skin area of the patient's body potions selected from the group consisting of abdomen, armpit, and limb.

According to another aspect, the processing of the skin 3D model comprises further removing at least one portion of the skin 3D model corresponding to at least one skin area of the patient's body potions selected from the group consisting of pubic region, densely populated hair region, and mouth.

According to another aspect, the processing of the skin 3D model comprises keeping a portion thereof corresponding to the patient's cheekbone.

According to another aspect, the processing of the skin 3D model comprises keeping a portion thereof corresponding to the patient's ear.

According to another aspect, a non-transitory storage medium storing a plurality of instructions executable by a computer is provided, wherein the plurality of instructions, when executed, causes the computer: to receive medical image data comprising a plurality of 2D cross-sectional images of a patient's body that encompasses a target tissue; to process the medical image data to generate a skin 3D model defining a 3D contour of the patient's skin; to receive information about the target tissue and information about a proposed medical procedure for treating or examining the target tissue; to identify one or both of (1) a first skin area of the patient that would contact or directly face a lying surface on which the patient would lie during the proposed medical procedure, and (2) a second skin area of the patient adjacent to a joint of the patient's body that would substantially change its position relative to the target tissue and/or substantially change its contour as a body part of the patient moves about the joint; and to remove, from the skin 3D model, one or both of (1) a first portion of the skin 3D model corresponding to the identified first skin area and (2) a second portion of the skin 3D model corresponding to the identified second skin area, thereby providing a skin marker for future use in real-time registration with images of the patient captured during the proposed medical procedure without use of an artificial physical marker fixed to or placed on the patient's body.

According to another aspect, the computer is a handheld computing device, wherein the plurality of instructions, when executed, further causes the handheld computing device: to capture the images of the patient while the patient is lying on a patient bed; to process the captured images of the patient and the skin marker to register them for augmented reality without use of an artificial physical marker fixed to the patient's body or worn by the patient; and to render, on the handheld computing device, a real-time augmented reality view comprising at least one of the plurality of 2D cross-sectional images of the patient's body superimposed on one or more additional images of the patient captured subsequent to the registration.

According to another aspect, the plurality of instructions, when executed, further causes the handheld computing device to render, on the handheld computing device, one or both of (a) a mesh of the skin 3D model and (b) a mesh of the skin marker.

BRIEF DESCRIPTION OF THE DRAWINGS

The foregoing and other features, aspects and advantages of the present invention are described in detail below with reference to the drawings of various implementations, which are intended to illustrate and not to limit the invention. The drawings comprise the following figures in which:

FIG. 1B illustrates a segmentation process during which skin contours are extracted from the medical images, according to an example implementation;

FIG. 1C illustrates how the skin contours in FIG. 1B are combined to generate a 3D model, according to an example implementation;

DETAILED DESCRIPTION

Figure 1A:
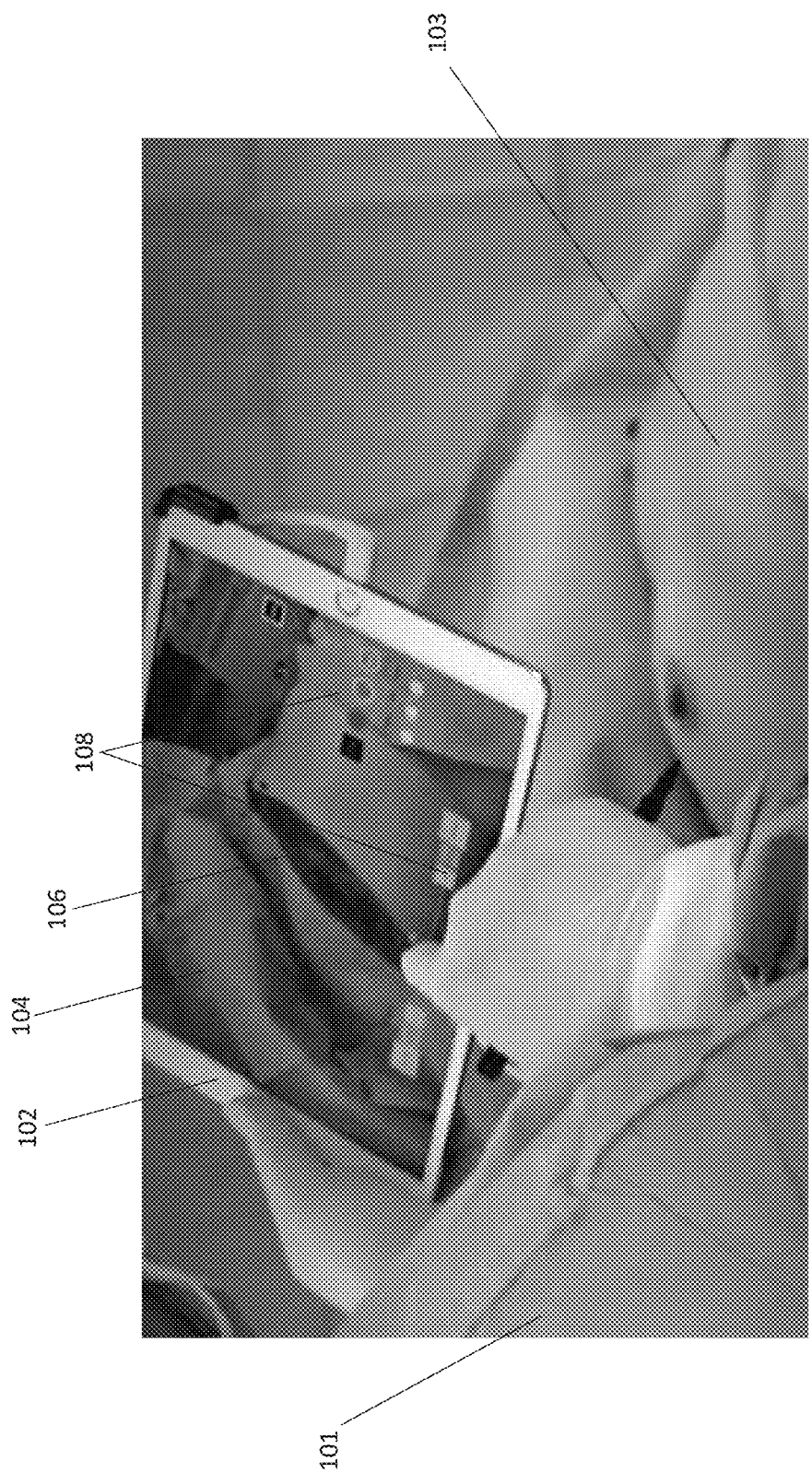
FIG. 1A illustrates a physician operating a computing device to view medical images of a patient superimposed over a real-time camera view displayed on the computing device, according to an example implementation.

Implementations of the invention will now be described with reference to the accompanying figures. The terminology used in the description presented herein is not intended to be interpreted in any limited or restrictive manner, simply because it is being utilized in conjunction with a detailed description of certain specific implementations of the invention. Furthermore, implementations of the invention may comprise several novel features, no single one of which is solely responsible for its desirable attributes or which is essential to practicing the inventions herein described.

Use of Augmented Reality (AR) in Medical Field

Augmented Reality (AR) refers to the insertion of virtual objects into real scenes. There are many attempts to provide augmented reality in the field of medicine. For example, a patient's medical images such as CT or Mill images (virtual objects) are superimposed with camera views of the patient (real scene) for AR that either the medical images alone or the camera views alone would not be able to offer. Medical professionals can use such AR in the context of medical procedure to understand the location and condition of tissues of interest under the skin without or before opening the patient's body for the procedure.

Registration

A key issue in AR is correct alignment of the virtual object with the real scene, which is called "registration". To facilitate the registration, an artificial object may be fixed to the patient's body such that the artificial object is included in the CT or Mill images and also in the camera views. Then, the artificial object is used as a reference called a marker for aligning the two. Alternatively, in some AR algorithms, no artificial object is used.

Registration without Artificial Marker

When no artificial object is used at the time of taking CT or MM images and also at the time of medical procedure, the registration relies on the patient's medical images obtained prior to the medical procedure and the images the camera captures at the time of the medical procedure. This may require a lot of computing power and a significant amount of time. In reality, however, AR for medical procedure requires real-time performance.

Registration Using Pre-Generated Marker

According to implementations of the invention, registration of a patient's CT or Mill images with camera views of the patient is performed without an artificial object fixed to the patient's body. Prior to the proposed medical procedure, the patient's CT or Mill images are processed to provide a body contour model (also referred to herein as a "3D model" or a "skin 3D model") that represents a skin contour of the patient's body or a portion thereof. The body contour model is processed to provide a skin marker that is a portion or portions of the body contour model that are selected for effective registration. In the foregoing processes, the patient's CT or MM images are already aligned with the body contour model and accordingly aligned with the skin marker as well. At the time of medical procedure, 3D images of the patient body or a portion thereof are captured using a camera. Then, the 3D images captured at the time of procedure are registered with the skin marker prepared in advance. Because the skin marker is already aligned with the patient's CT or MM images, the registration between the 3D images and the skin model will correctly align the patient's CT or MM images with the camera views presented on the camera. Then, the patient's CT or MRI images (virtual object) can be superimposed with the camera views (real scene).

After Successful Registration, Medical Images can be Displayed Over Camera View

FIG. 1A illustrates an example use case after the registration described above has been completed using the techniques of the present disclosure, which are described in greater detail below with reference to FIGS. 1B-7. In FIG. 1A, a physician 101 a physician 101 is operating a computing device 102 that has a camera pointed at a patient 103 who is lying on a surgical bed. The computing device 102 displays a real-time camera view 104 of the patient 103 as well as a medical image 106 superimposed over a specific section of the patient's body in the real-time camera view 104. The computing device 102 also displays a plurality of user interface controls 108 that the physician 101 can use to navigate to other medical images of the patient corresponding to other sections of the patient's body in the real-time camera view 104. Although not shown in FIG. 1A, the medical image superimposed over the real-time camera view may indicate the presence and specific location of a lesion underneath the user's skin and/or the distance from the patient's skin to the location of the lesion. Using the information provided by the medical images superimposed over the real-time camera view, the physician 101 can plan out the medical procedure (e.g., make appropriate markings on the patient's body, decide where to make an incision, etc.) much more effectively than having to view such medical images on a separate screen that does not also show the real-time view of the patient.

Medical Procedures

As used herein, the phrase "medical procedure" refers to any procedure that is performed by a medical professional such as a physician. The techniques described herein can be applied in a variety of different medical and surgical settings. For example, in some implementations, the techniques can be applied to medical procedures such as surgeries in the patient's brain, liver, pancreas, abdominal organs, and blood vessels, soft organs such as breasts, as well as other applications such as endoscopies, bronchoscopies, and the like.

Medical Image

As used herein, the phrase "medical image" refers to any image of the patient that is generated prior to the medical procedure and is referenced by the physician while preparing for the medical procedure or during the medical procedure. Although CT and MRI images are used herein as examples, in other implementations, other images may be used.

Computing Device

The computing device 102 used by the physician 101 in FIG. 1A can include any computing device with a camera and a display, including, but not limited to, a smartphone, tablet computer, head-mounted display, desktop computer, laptop computer, wearable device, and the like. As described in greater detail below, the pre-generated skin marker simplifies the registration process such that the registration as well as the superimposition can be performed in real time by a portable, handheld computing device. In some implementations, the computing device 102 does not include one or neither of a camera and a display, and communicates with such component(s) via wired or wireless connection to implement the techniques described herein.

Registration Involves Aligning Coordinate Systems

The registration described herein involves aligning the coordinate system used by the 3D model (also referred to herein as the "3D model coordinate system") with the coordinate system used by the computing device 102 (also referred to herein as the "computing device coordinate system") such that specific locations within the real-time camera view provided by the computing device 102 can be associated with corresponding locations in the 3D model and therefore with corresponding medical images and further such that changes in the camera location and angle would result in corresponding changes in the size and angle of the medical images superimposed over the camera view.

Improved Registration Involving Pre-Processing and Runtime Processing

Registering the 3D model coordinate system to the computing device coordinate system and superimposing the medical images over the real-time camera view may include, for example, the steps performed prior to the patient being prepared for the medical procedure (pre-processing) such as generating a 3D model using the medical images of the patient and generating a skin marker using the 3D model by removing specific portions of the 3D model, and the steps performed as the patient is being prepared for the medical procedure or during the medical procedure (runtime processing) such as aligning the pre-generated skin marker with the images of the patient (e.g., images of the patient lying on the surgical bed) and displaying the medical images as superimposed over the real-time camera view of the computing device 102. Because the 3D model and the skin marker are generated in advance (and not at runtime), using the techniques described herein, the time and computing resources needed to perform the registration and superimposition at runtime can be reduced, thereby enabling and improving the real-time experience provided to the operator.

Initiating Pre-Processing of Medical Images

One or more medical images of the patient such as CT or MRI images may be taken to visualize the inside of the patient's body. If the conditions shown by the medical images necessitate a medical procedure that would benefit from superimposing the medical images over a real-time view of the patient, the pre-processing of the medical images may be initiated, to facilitate such superimposing of medical images, an example of which is shown in FIG. 1A.

Pre-Processing of Medical Images

Figure 2B:
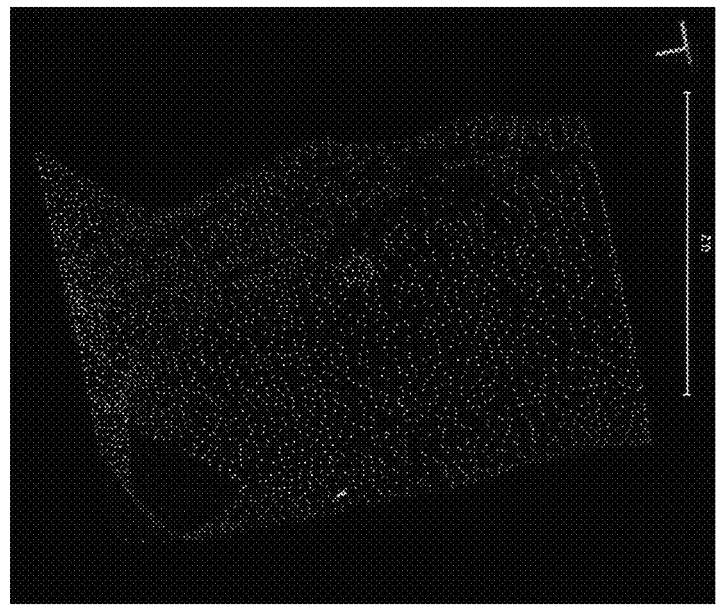
FIG. 2B illustrates a downsampled version of FIG. 2A, according to an example implementation.

In some implementations, the pre-processing of the medical images includes a segmentation process during which the skin contour of the patient's body (e.g., outline of the outer surface of the patient depicted in the medical image) is extracted from each of the medical images (e.g., as illustrated in FIG. 1B), and a 3D modeling process during which the extracted skin contours are used to generate a 3D point cloud (e.g., as illustrated in FIG. 2B). The 3D point cloud is also referred to herein as a "3D model".

Segmentation Process

As illustrated in FIG. 1B, the segmentation process may include, according to an implementation, filtering, representing the filtered data in a histogram, thresholding to identify the portions of the filtered data corresponding to the patient's body, refining segmentation, and performing edge extraction. Although specific methods and algorithms are used as examples below, one of ordinary skill in the art would appreciate that other techniques may be used. One of more of the steps described herein may be omitted or switched with another step, and one or more additional steps not described herein may be added.

Filtering

The filtering step reduces noise in the data included in the medical image (also referred to herein as the "medical image data"). Gaussian filtering, anisotropic diffusion filtering (ADF), and/or other techniques may be used.

Thresholding

The thresholding step uses a certain threshold (e.g., pixel intensity level) to segment images. For example, the thresholding step may include representing the filtered medical image data in a histogram and distinguishing the portions of the medical image data corresponding to the patient's body from the portions of the medical image data corresponding to the background (e.g., regions outside the patient's body, or empty space) using Otsu's method. Although Otsu's method is used as an example, other techniques may be used.

Refining Segmentation

The refining step refines the segmented region. For example, the refining step may include performing seeded region growing (SRG) segmentation and morphological segmentation. For example, the SRG segmentation and the morphological segmentation can be performed in sequence. Although SRG and morphological segmentation are used as examples, other techniques may be used.

Edge Extraction

The edge extraction step extracts the skin contour from the refined segmented region. As shown in FIG. 1B, from the refined segmented region illustrated in the fifth image of FIG. 1B, the outer edges that correspond to the skin contour of the patient for the specific cross-section of the patient's body corresponding to the medical image may be extracted. For example, any known edge detection and extraction algorithms may be used.

3D Modeling

Figure 2A:
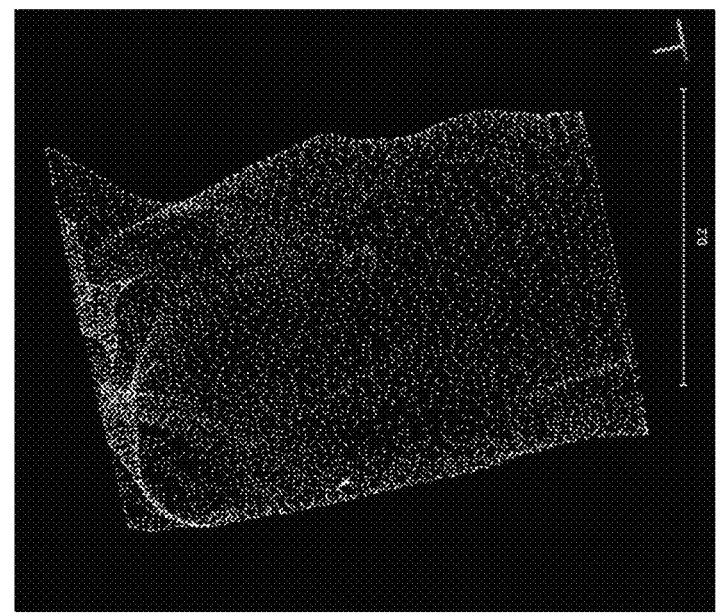
FIG. 2A illustrates a collection of pixels extracted from the segmentation process of FIG. 1B, according to an example implementation.

The 3D modeling process includes combining the skin contours extracted from the segmentation process described above (e.g., the outer edges extracted from each medical image) to generate a 3D model (e.g., the images shown in FIGS. 2A and 2B). The 3D modeling process is described in greater detail below with reference to FIGS. 2A-3B.

Collection of Vertices

FIG. 2A illustrates a collection of vertices (e.g., the angular points in the skin contour of each medical image) extracted from the segmentation process of FIG. 1B, according to an example implementation. For example, the skin contour extracted from the segmentation process may include a plurality of vertices, and a point cloud may be generated by combining all of the vertices from all of the medical images pre-processed as described herein. The point cloud is illustrated in FIG. 2A.

Vertex Coordinate Values

Each vertex in the point cloud may be associated with a set of coordinate values in a 3D coordinate system (e.g., a set of x-axis, y-axis, and z-axis coordinate values in a coordinate system associated with the medical images). In other implementations, each vertex is not associated with an explicit set of coordinate values, and the positions of the vertices are determined based on their relative positions in the data structure (e.g., the point cloud).

Downsampling of Vertices

The vertices in the point cloud may be downsampled to reduce the number of data points and computations and to reduce the complexity of generating the 3D model based on the vertices in the point cloud. FIG. 2B illustrates a downsampled version of the point cloud shown in FIG. 2A. For example, the number of vertices may be reduced by about one-tenth (e.g., from about 100,000 vertices to about 10,000).

Normal Vectors

The normal vector of each of the vertices included in the point cloud illustrated in FIG. 2A may be calculated for use in generating the 3D model, for example, by filling in the gap between the vertices in the downsampled point cloud.

Meshing

Meshing facilitates visualization of the 3D model by generating a 3D geometric object using the vertices and/or the vectors of the 3D model (e.g., 3D point cloud). As illustrated in FIGS. 1C, 3A, 3B, 4A, 4B, 5A, and 5B, the meshing process makes it easier to visualize the 3D model or the skin marker generated based on the 3D model.

Mesh Examples

Figure 3A:
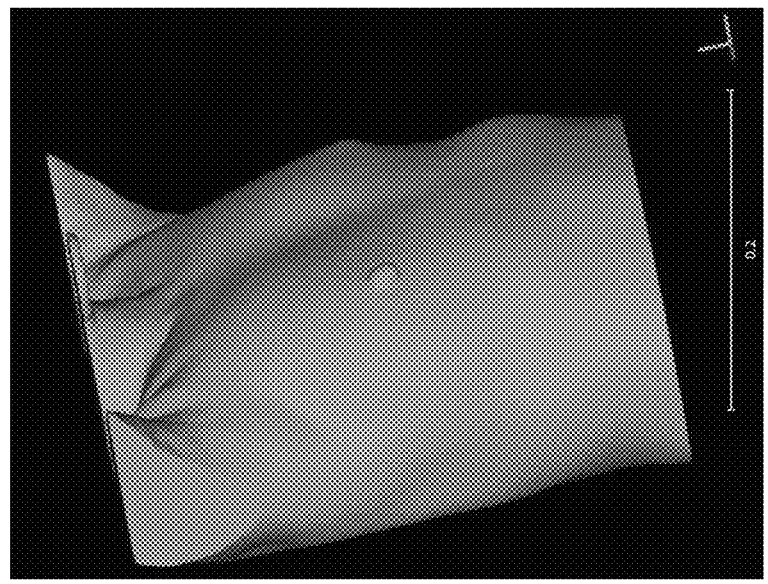
FIG. 3A illustrates a 3D model generated using the collection of pixels in FIG. 2B, according to an example implementation.

FIG. 3A illustrates a mesh generated based on the 3D model shown in FIG. 2B. For example, the mesh may be generated using the 3D discrete scalar field (also referred to herein as voxel data) of the 3D model shown in FIG. 2B, according to an example implementation. For example, the marching cubes algorithm can be used to generate the mesh. In some implementations, a Fast-Quadric Mesh Simplification algorithm can be used to simply the generation of the mesh, thereby reducing the consumption of computing resources. In other implementations, one or more other algorithms (e.g., mesh decimation, mesh simplification, etc.) are used instead.

Smoothing

Figure 3B:
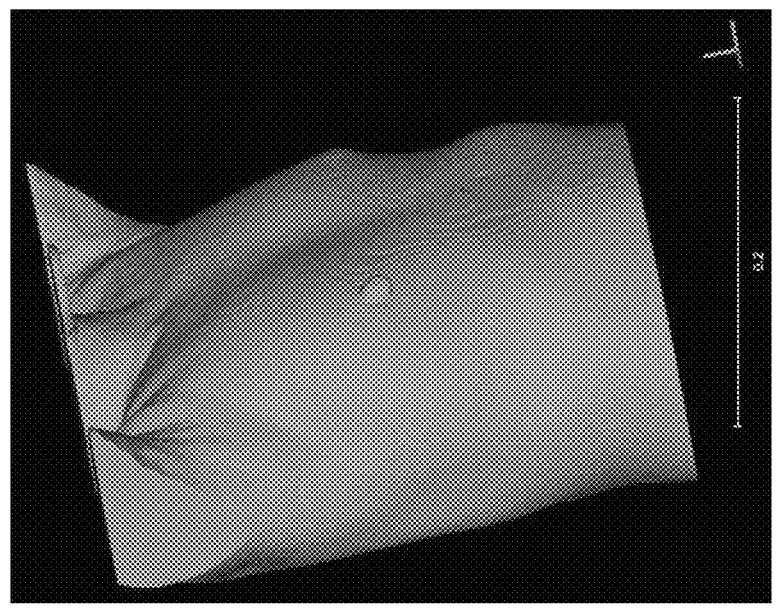
FIG. 3B illustrates a smoothed version of FIG. 3A, according to an example implementation.

Smoothing is a technique used to capture significant patterns in a data set while leaving out noise or other fine-scale characteristics. FIG. 3B illustrates a smoothed version of FIG. 3A, according to an example implementation. For example, a Gaussian filter may be used to smooth the mesh shown in FIG. 3A. In other implementations, one or more other smoothing filters are used.

Illustration of 3D Models Using Meshes

The 3D models described herein may be illustrated using the meshes generated based on the 3D models. For example, FIGS. 3A-5B each illustrate the mesh corresponding to the underlying 3D model (or a portion thereof, which is also referred to herein as a "skin marker").

Generation of Tissue 3D Model

Using the same or similar process described above for generating the 3D model representing the skin contour of the patient, another 3D model representing the tissue or region of interest inside the patient's body may be generated. Such 3D model may be referred to herein as a "tissue 3D model".

Additional Details of Segmentation, Meshing, Smoothing, Matching, and Registration Additional details relating to segmentation, meshing, smoothing, matching, registration, and other techniques described herein are provided, for example, in International App. Pub. No. WO2005/088539, titled "AUGMENTED REALITY SYSTEM WITH COREGISTRATION OF VIRTUAL OBJECTS ON IMAGES OF REAL OBJECTS," U.S. Pat. No. 9,498,132, titled "VISUALIZATION OF ANATOMICAL DATA BY augmented REALITY," U.S. Pat. App. Pub. No. 2018/0114325, titled "SYSTEMS AND METHODS FOR DETERMINING QUALITY METRICS OF AN IMAGE OR IMAGES BASED ON AN EDGE GRADIENT PROFILE AND CHARACTERIZING REGIONS OF INTEREST IN AN IMAGE OR IMAGES," U.S. Pat. App. Pub. No. 2017/0161945, titled "KEYPOINT-BASED POINT-PAIR-FEATURE FOR SCALABLE AUTOMATIC GLOBAL REGISTRATION OF LARGE RGB-D SCANS," and U.S. Pat. No. 10,603,118, titled "METHOD FOR RECOVERING PATIENT REGISTRATION," the disclosures of which are incorporated herein by reference in their entirety for all purposes. In addition to the techniques described herein and the aforementioned disclosures, other techniques known to one of ordinary skill in the art may be used.

Generation of Skin Marker from 3D Model

Using the 3D model generated from the medical images via the processes described above, the computing device 102 generates a skin marker prior to the patient being prepared for the medical procedure. By removing portions of the 3D model that would interfere with or delay the registration process performed at runtime (e.g., during the preparation for the medical procedure or during the medical procedure), the pre-generated skin marker can expedite the registration process and improve the accuracy of the registration, thereby providing a real-time performance suitable for medical procedures.

Who Generates Skin Marker

In some implementations, a computing device generates the skin marker based on input from a medical professional. For example, the 3D model may be displayed on a display screen of the computing device, and the medical professional may select, via touchscreen controls or physical controls, portions of the 3D model to be removed. The portions of the 3D model that remain after all the removal may be used as the skin marker. In other implementations, an automated computing software generates the skin marker. For example, the automated computing software may determine, based on the medical images and/or the 3D model, which portions of the 3D model should be removed and removes them, thereby generating the skin marker. The portions of the 3D model that the medical professional and/or the automated computing software may decide to remove from the 3D model are described in greater detail below.

Skin Marker is not Artificial

In some implementations, the skin marker does not include a marker that is artificially introduced into the medical images. For example, the skin marker is generated by keeping or removing portions of the 3D model that correspond to natural features of the patient (e.g., joint, bone, hair, etc.) depicted in the medical images, without the aid of an artificial marker introduced into the medical images and/or the 3D model (e.g., by introducing a physical or virtual object or marking onto or into the patient's body prior to capturing the medical images) for the purpose of facilitating the registration process described herein. In other implementations, the skin marker is generated based at least in part on an artificial marker introduced into the medical images.

Registration without Artificial Markers Typically Less Accurate

In typical implementations not using artificial markers and relying solely on the natural features of the patient, aligning the 3D model with the 3D images of the patient captured at runtime is less accurate due to the presence of noise that can interfere with the alignment process. For example, the positions of the patient's various body parts may have changed (e.g., arms down vs. arms up, full vs. empty stomach) between the time when the medical images are taken and the time when the patient has been prepared for the medical procedure (e.g., when the patient is positioned on the surgical bed for a surgery). As another example, some of the patient's body parts shown in the medical images may not be shown in the 3D images taken at runtime due to such portions being covered (e.g., by the surgical drapes) or otherwise hidden or facing away from the camera view (e.g., the patient's back touching the surgical bed, in the case of a chest surgery). Thus, in such implementations, the likelihood of an erroneous alignment and/or registration is increased.

Registration without Artificial Markers Typically Consume More Resources

Additionally, in typical implementations not using artificial markers and relying solely on the natural features of the patient, aligning the 3D model with the 3D images of the patient captured at runtime may consume a greater amount of time and/or computing resources because the unavailability of artificial markers may result in more guesswork on the part of the computing device performing the alignment. Thus, in such implementations, more time and computing resources are needed to provide an adequate alignment between the 3D model and the 3D images. Accordingly, real-time performance is difficult to achieve without an artificial marker.

Improved Skin Marker

In the implementations of the present disclosure, a skin marker is generated by removing portions of the 3D model that would potentially interfere with or delay the registration process (such as the movable or invisible portions of the patient's body described herein). By doing so, the likelihood of an inaccurate alignment/registration may be reduced. Additionally or alternatively, the amount of time and computing resources consumed during the registration process may be reduced.

Noise Portions of 3D Model that May Interfere with Registration

In some implementations, certain portions of the 3D model that may interfere with or delay the registration process to be performed at runtime is determined (e.g., by a human operator, the computing device 102, or another computing device different from that used to provide real-time views at runtime). Such portions can include (i) one or more portions of the 3D model that correspond to portions of the patient's body that may be shown in the medical images but not in the images of the patient's body at runtime (e.g., after the patient has been prepared for surgery and is lying on the surgical bed), and (ii) one or more portions of the 3D model that correspond to portions of the patient's body that can be moved or re-positioned between the time when the medical images are taken and the time when the patient is positioned for the medical procedure. Such portions may also be referred to herein as "noise portions". The noise portions are described in greater detail below with reference to FIGS. 4A-5C.

Identifying Noise Portions

In some implementations, a target body part for the medical procedure is identified, for example, by a human operator via a user interface provided by a computing device, or automatically by a computing device based on the medical images. The identified target body part may be the portion of the patient's body including a region of interest for the medical procedure, such as a tissue or lesion that needs to be examined or treated. For the identified target body part, certain predetermined body parts that are known to potentially interfere or delay (due to potentially being invisible or movable in the patient's images captured at runtime) the registration are removed from the 3D model to generate the skin marker. For example, portions of the 3D model that correspond to one or more joints connected to the target body part (e.g., patient's torso) may be removed (e.g., joints in the shoulder/armpit region). As another example, portions of the 3D model that correspond to portions of the patient's body adjacent to such joints may be removed (e.g., the skin area near the joints in the shoulder/armpit region). As yet another example, portions of the 3D model that correspond to portions of the patient's body connected to the target body part via such joints may be removed (e.g., arms connected to the patient's torso via the joints in the shoulder/armpit region).

Additional Examples of Identified Noise Portions

For a brain surgery, the portions of the 3D model corresponding to the patient's neck and below (position can change) and hair (patient may be wearing a hair cap) may be removed. For a lung biopsy, the portions of the 3D model corresponding to the patient's neck and above (position can change), shoulder joints and arms (position can change), abdomen (patient may have been fasting), and hip joints and below (position can change) may be removed the removed.

Determination of Medical Procedure

In some implementations, the skin marker generation process is specific to the medical procedure. The medical procedure may be determined by a human operator and/or inputted into the computing device performing the skin marker generation process. As another example, the computing device performing the skin marker generation process may automatically determine the medical procedure without human input based on the medical images. In other implementations, the skin marker generation process is not specific to the medical procedure.

Removing Invisible or Obstructed Portions

In some implementations, when generating the skin marker from the 3D model, one or more portions of the 3D model that correspond to portions of the patient's body that may be shown in the medical images but not in the images of the patient's body at runtime (e.g., after the patient has been prepared for surgery and is lying on the surgical bed) are removed. Such portions may include the patient's back (in the case of a chest surgery), chest (in the case of a back surgery), body parts facing the surgical bed, body parts not relevant to the medical procedure (since such body parts may be covered up with surgical drapes), body parts that would be covered during the medical procedure (e.g., hair, eyebrows, etc.), body parts facing away from the surgeon, and the like. Such portions may also be referred to herein as "noise portions".

Not all Invisible or Obstructed Portions Need to be Removed

In some implementations, not all of the potentially invisible or obstructed portions are removed from the 3D model when generating the skin marker. For example, if the 3D depth scanning of the patient at runtime (described in greater detail below) occurs prior to the patient being covered up for the medical procedure, portions of the 3D model that correspond to the patient's body parts that would be covered up during the medical procedure may remain in the skin marker. Such portions may be used to align the skin marker to the 3D images of the patient. In other implementations, all of the potentially invisible or obstructed portions are removed from the 3D model when generating the skin marker.

Example of Invisible or Obstructed Portions (Patient's Back)

Figure 4A:
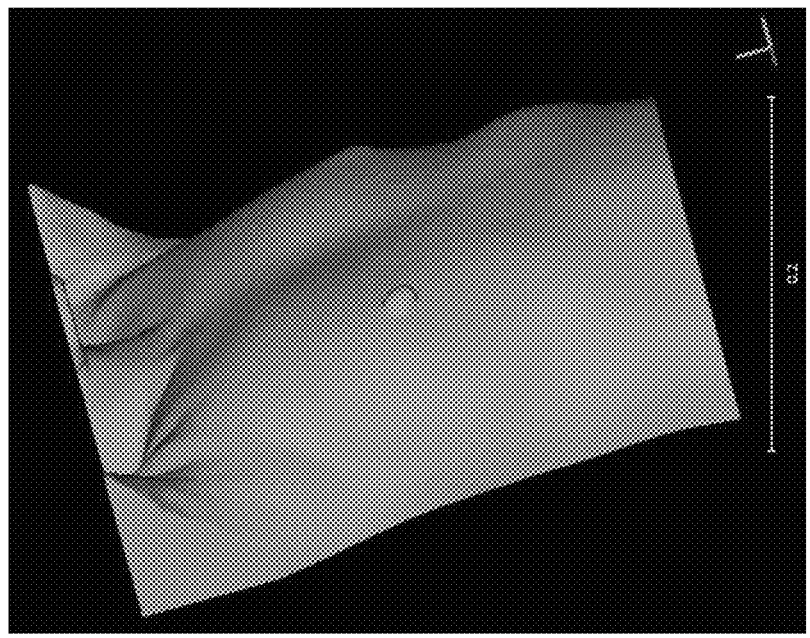
FIG. 4A illustrates the result of removing the patient's back portion from the 3D model of FIG. 3B, according to an example implementation.

FIG. 4A illustrates the result of removing the patient's back portion from the 3D model of FIG. 3B, according to an example implementation. As shown in FIG. 4A, the portions of the 3D model corresponding to the user's back have been removed, since the patient's back may be visible in the medical images taken prior to runtime but invisible in the 3D images captured at runtime.

Removing Movable Portions

In some implementations, when generating the skin marker from the 3D model, one or more portions of the 3D model that correspond to portions of the patient's body that can be moved or re-positioned from the time when the medical images are taken to the time when the patient is positioned for the medical procedure (e.g., when the patient is on the surgical bed for a surgery) are removed. For example, if the patient took the MRI images with her arms down but will undergo the surgery with her arms up, the portions of the 3D model corresponding to her arms would not be helpful in (and could even interfere with) aligning the 3D model with the images of the patient at runtime, because the orientations of her arms would be different in the 3D model and in the images (e.g., due to the presence of joints). As another example, if the patient took the MRI images with a full stomach but will undergo the surgery with an empty stomach, the portions of the 3D model corresponding to her abdomen would not be helpful in (and could even interfere with) aligning the 3D model with the images of the patient at runtime, because the size and shape of her abdomen would be different in the 3D model and in the images. As yet another example, if the medical procedure involves intubation, the openings through which tubes would be inserted may be removed (e.g., nose or mouth). As yet another example, gravity and/or change in posture may affect the shape and position of the patient's body parts, and such body parts may be removed (e.g., breast, male genitalia, etc.). Such portions may also be referred to herein as "noise portions".

Not all Movable Portions Need to be Removed

In some implementations, not all of the movable portions are removed from the 3D model when generating the skin marker. For example, if a portion of the 3D model corresponds to a movable body part of the patient, but the movable body part is not expected to be positioned differently during the medical procedure with respect to the time at which the medical images were captured, such portion may not be removed and remain part of the skin marker. Such portion can thus be used to align the skin marker to the 3D images of the patient. In other implementations, all of the movable portions are removed from the 3D model when generating the skin marker.

Joint

As used herein, the term "joint" refers to an area where two bones of an animal skeleton are attached for the purpose of allowing the two bones to move about the area. For example, the joints in the human body may include pivot joints such as those found between the neck vertebrae, hinge joints such as those found in the elbows, ankles, fingers, toes, and knees, saddle joints such as those found in the thumbs, plane joints such as those found in the wrists and ankles, condyloid joints such as those found in the wrists and arms, and ball-and-socket joints such as those found in the shoulders and hips.

Movable Joints

A typical human body includes over 200 joints, some of which may be immovable. In some implementations, only movable joints represented in the 3D model are removed from the 3D model when generating the skin marker. In other implementations, all joint represented in the 3D model are removed from the 3D model when generating the skin marker. In other implementations, only a subset of the movable joints represented in the 3D model is removed from the 3D model when generating the skin marker.

Example of Movable Portions (Patient's Joints)

In some implementations, the body part depicted in the medical images (e.g., head, chest, abdomen, lower body, etc.) is identified, and the skin marker is generated by removing, from the 3D model, all the portions corresponding to the joints specific to the identified body part. For example, if it is determined that the medical images depict the patient's head, the skin marker may be generated by removing the portions of the 3D model corresponding to the joints in the patient's head such as the lower jaw and the upper jaw. As another example, if it is determined that the medical images depict the patient's chest, the skin marker may be generated by removing the portions of the 3D model corresponding to the joints near the patient's chest such as the joint in the shoulders, also known as the glenohumeral joint.

Direction in which Joints are Removed

In some implementations, the portions of the 3D model corresponding to the patient's joints and the patient's body part on the other side of the joints are removed from the 3D model as part of generating the skin marker. For example, if the region of interest of the medical procedure is in the patient's chest, the shoulder joints and the arms may be removed. On the other hand, if the region of interest of the medical procedure is in the patient's upper arm, the shoulder joints and the chest may be removed. As another example, if the region of interest of the medical procedure is in the patient's upper leg (above the knee), the knee joints and the lower leg may be removed. On the other hand, if the region of interest of the medical procedure is in the patient's lower leg (below the knee), the knee joints and the upper leg may be removed.

Example of Movable Portions (Patient's Armpits)

Figure 4B:
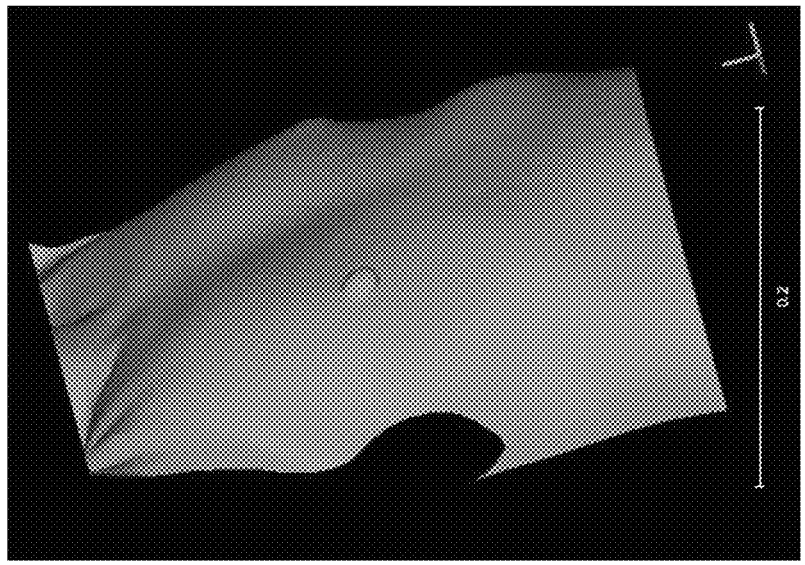
FIG. 4B illustrates the result of removing the patient's arm portions from the 3D model of FIG. 4A, according to an example implementation.

FIG. 4B illustrates the result of removing the patient's armpit portions from the 3D model of FIG. 4A, according to an example implementation. As shown in FIG. 4B, the portions of the 3D model corresponding to the user's armpits have been removed, since the position of the patient's arms may change from the medical images taken prior to runtime to the 3D images captured at runtime.

Another Example of Movable Portions (Patient's Abdomen)

Figure 5C:
FIG. 5C illustrates an image of the patient taken on the surgical bed, according to an example implementation.
Figure 5B:
FIG. 5B illustrates the result of removing the patient's left chest portion from the 3D model of FIG. 5A, according to an example implementation.
Figure 5A:
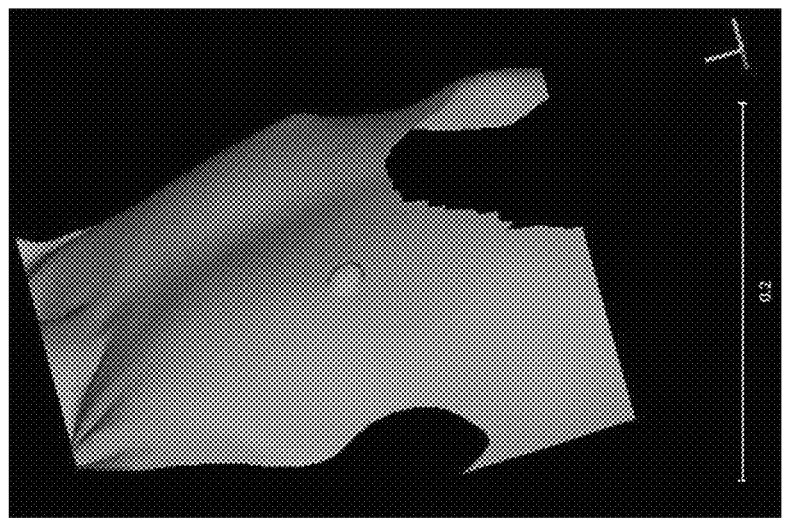
FIG. 5A illustrates the result of removing the patient's abdomen portion from the 3D model of FIG. 4B, according to an example implementation.

FIG. 5A illustrates the result of removing the patient's abdomen portion from the 3D model of FIG. 4B, according to an example implementation. As shown in FIG. 5A, the portions of the 3D model corresponding to the user's abdomen have been removed, since the patient's abdomen may look different in the medical images taken prior to runtime and the 3D images captured at runtime.

Another Example of Invisible or Obstructed Portions (Patient's Opposite Chest)

FIG. 5B illustrates the result of removing the patient's left chest portion from the 3D model of FIG. 5A, according to an example implementation. As shown in FIG. 5B, the portions of the 3D model corresponding to the user's left chest (e.g., opposite side of the right chest undergoing surgery) have been removed, since the patient's left chest may be visible in the medical images taken prior to runtime but invisible in the 3D images captured at runtime due to being covered by the surgical drapes (e.g., as shown in FIG. 5C).

Identifying Portions of 3D Model for Removal

In some implementations, the portions of the 3D model to be removed (e.g., regions of the 3D model corresponding to the patient's body parts expected to be invisible or moved in the 3D images taken at runtime) are predetermined for the medical images (e.g., for chest CT images or 3D models near the chest region, remove the patient's armpits, for head CT images or 3D models near the head region, remove the patient's jaws, etc.). In other implementations, such portions are determined based on user input (e.g., operator of the computing device 102 selects one or more portions of the 3D model for removal). In yet other implementations, some of such portions are predetermined and the remaining ones of such portions are determined based on user input.

Target Portions of 3D Model that are Included in Skin Marker

In some implementations, as part of determining which portions of the 3D model should be kept in the skin marker, the location of the target of interest in the medical procedure (e.g., lesion) in the medical images is determined. Using the location of the target of interest, the bone(s) nearest to the target of interest is/are identified. Then, the portions of the 3D model corresponding to the skin alongside the identified bone(s) may be included in the skin marker. Such portions are unlikely to change in position or shape between the time when the medical images are taken and the time when the patient has been prepared for the medical procedure. Therefore, such portions are used as part of the skin marker to facilitate alignment and registration described herein. Such portions may include the patient's clavicle, sternum, ribcage, ribs, cheekbones, ears, etc. Such portions are also referred to herein as "target portions".

Target Portions May not Include Skin Area Closest to Region of Interest

In some implementations, the skin alongside the bone(s) nearest to the target of interest (e.g., lesion) to be included in the skin marker as described above is farther away from the skin that is nearest to the target of interest. In such implementations, the skin nearest to the target of interest may not be included in the skin marker (e.g., because the skin is considered a noise portion, which is described in greater detail below, that would interfere with the registration process). For example, if the target of interest is in the patient's abdomen, the nearest bone may be the sternum or the lowest rib, and the skin alongside such bone would be closer to the chest of the patient and would be farther away from the region of interest than, for example, the skin on the patient's abdomen. In other implementations, the skin marker includes the skin of the patient nearest to the target of interest.

Skin Marker Generation Based on Target Portions and Noise Portions

In some implementations, the skin marker includes only the target portions described herein. In such implementations, the skin marker is generated by identifying the target portions as described herein and removing all other portions from the 3D model. In other implementations, the skin marker includes only those portions of the 3D model that are not removed as being noise portions. In such implementations, the skin marker is generated by identifying the noise portions as described herein and removing all of the identified noise portions from the 3D model. In yet other implementations, the skin marker includes an intersection (e.g., in both sets) of the identified target portions and those portions not removed as being noise portions. In yet other implementations, the skin marker includes a union (e.g., in either set) of the identified target portions and those portions not removed as being noise portions.

Not all Portions of Skin Marker May be Contiguous

In some implementations, the skin marker includes two portions that are not touching or neighboring each other. For example, the skin marker may include one piece near the patient's lowest rib, and another piece near the patient's clavicle, where the two pieces are not connected and are entirely separated from each other. In other implementations, the entire skin marker is a single piece of the 3D model (e.g., as shown in FIG. 5B).

Skin Marker Generation Process Specific to Medical Procedure

In some implementations, the portions of the 3D model removed to generate the skin marker differ depending on the medical procedure. For example, for a chest surgery, the back portion of the 3D model may be removed (since the back will be touching the surgical bed during the surgery and thus not in the camera view of the patient), whereas for a back surgery, the chest portion of the 3D model may be removed (since the chest will be touching the surgical bed during the surgery and thus not in the camera view of the patient). The medical procedure and/or the portions to be removed may be specified by the operator (e.g., the physician performing the medical procedure) of the computing device 102 or another computing device different from that used to provide real-time views at runtime. In other implementations, the portions of the 3D model removed to generate the skin marker are determined without considering the specific medical procedure to be performed (e.g., by removing only universally distracting features such as joints, abdomen, etc.).

Example Skin Marker Generation for Neurosurgery

In the example of a neurosurgical procedure involving the patient's skull, the portions of the 3D model corresponding to invisible or movable features of the patient can be removed, such as the patient's jaw (since its shape may change due to the presence of joints), mouth (since its shape may change due to intubation through the mouth), nose (since its shape may change due to intubation through the nose), hair (since it will be covered by the hair cap worn by the patient), eyebrow (since it can be covered during the surgery), forehead (since it can be covered during the surgery), and the like, thereby leaving only those portions of the 3D model corresponding to the visible but immovable features of the patient in the skin marker, such as the cheekbones, cheeks, ears, and the like, and the connecting portions therebetween.

Processing Performed at Runtime

As described above, registering the 3D model coordinate system to the computing device coordinate system and superimposing the medical images over the real-time camera view may include certain steps that are performed as the patient is being prepared for the medical procedure or during the medical procedure (runtime processing) such as aligning the pre-generated skin marker with the images of the patient (e.g., images of the patient lying on the surgical bed) and displaying the medical images as superimposed over the real-time camera view of the computing device 102. These processes are described in greater detail below.

Accessing Medical Images, 3D Model, and Skin Marker

At runtime, the computing device 102 accesses the medical images of the patient, the 3D model generated based on the medical images, and/or the skin marker generated based on the 3D model. In some implementations, one or more of the medical images, 3D model, and skin marker are accessed from an internal storage device of the computing device 102.

In other implementations, one or more of the medical images, 3D model, and skin marker are accessed from an external storage device (e.g., via wired or wireless communication).

3D Depth Scanning of Patient

At runtime, the computing device 102 scans the patient using a 3D depth camera, and uses the data generated by the 3D depth camera to register the coordinate system of the skin marker with the coordinate system of the computing device 102. For example, the physician performing the medical procedure on the patient may point the 3D depth camera connected to the computing device 102 at the patient lying on the surgical bed and initiate the scanning process (e.g., by providing a user command via a digital button provided on the display screen of the computing device 102).

Data Captured During 3D Depth Scanning

During the scanning, the computing device 102 causes the 3D depth camera of the computing device 102 (e.g., integrated into the computing device 102 or externally connected to the computing device 102) to capture one or more 3D images of the patient's body. Each 3D image may be associated with (i) one or more objects depicted therein and their corresponding depths, (ii) the orientation of the computing device 102 at the time of capturing the 3D image (e.g., the direction in which the 3D depth camera is pointed), and (iii) the position of the computing device 102 at the time of capturing the 3D image (e.g., the location of the computing device 102 in the 3-dimensional space).

Use of Markers at Runtime

In some implementations, one or more markers are fixed to or placed on the patient's body to facilitate the registration process. For example, such a marker would appear in the 3D images of the patient captured at runtime, and the indication of the marker would mapped to a specific portion of the skin marker and/or would be used as a reference point during the registration process. In other implementations, such markers are not used at runtime, and the 3D scanning and/or the registration described herein are performed without a visible marker fixed to or placed on the patient's body.

Timing of 3D Depth Scanning

In some implementations, the scanning takes place after the patient has been positioned for the medical procedure (e.g., placed on the surgical bed for a surgery) but before the patient's body is covered up for the medical procedure (e.g., before the patient is covered up as shown in FIG. 5C). In other implementations, the scanning takes place after the patient has been positioned for the medical procedure (e.g., after the patient has been placed on the surgical bed for a surgery) and after the patient's body is covered up for the medical procedure (e.g., after the patient is covered up as shown in FIG. 5C).

Amount of 3D Images Captured

In some implementations, the computing device 102 continuously captures 3D images of the patient and analyzes the captured 3D images in real time until the registration process is completed. In some implementations, the computing device 102 captures a fixed number of 3D images of the patient and performs the registration process based on the captured 3D images.

Registering 3D Model Coordinate System to User Computing Device Coordinate System Implementations of the present disclosure relate to systems and techniques for registering a coordinate system associated with the 3D model (and thus aligned with the medical images as well as the skin marker) with another coordinate system used by a computing device (e.g., a tablet computer operated by the physician in the operating room). Thus, registration can be used by the AR system of the present disclosure to determine the 3D location associated with each medical image of the patient within the real-time camera view provided by the computing device.

Matching Features

Registration can be performed by identifying matching points/regions in the pre-generated skin marker and the 3D images (or a 3D model generated based on the 3D images) of the patient captured at runtime (e.g., as the patient is lying on the surgical bed). In some implementations, a point pair feature (PPF) algorithm is used. In other implementations, one or more other 3D matching algorithms are used instead. In some implementations, an iterative closest point (ICP) algorithm is used to improve the accuracy of the registration process.

Superimposing Medical Images Over Real-Time Camera View

After registration, the computing device 102 can display medical images superimposed over the real-time camera view 104 displayed on the display of the computing device 102, as illustrated in FIG. 1A. For example, the computing device 102 displays the medical images, one at a time, over corresponding positions (e.g., based on the registration) on the patient's body in response to user input. The size and orientation of the superimposed medical images may change as the position and orientation of the camera of the computing device 102 changes. The computing device 102 may also indicate, on the real-time camera view displayed on the display, the location of the region of interest in the superimposed medical images and the distance between the region of interest and the nearest skin of the patient.

Using Superimposed Medical Images

By scrolling through the medical images, the physician 101 can identify the medical image showing the region of interest (e.g., lesion), and make certain decisions on how to perform the medical procedure. For example, the physician 101 may cause (e.g., using the user interface controls 108) one of the medical images that shows the tumor inside the patient's breast to be displayed on the display, and determine the location on the patient's breast at which an incision should be made for removing the tumor (e.g., one that would provide easiest and/or closest access to the tumor).

Data Superimposed on Camera View of Patient

Although some implementations described herein describe superimposing one or more medical images (e.g., a medical image showing a lesion or region of interest) on the real-time camera view or one or more images/photographs of the patient captured at runtime, additionally or alternatively, other data may be superimposed on the real-time camera view or the images/photographs of the patient such as (i) the skin marker or a portion thereof, (ii) the 3D model or a portion thereof, (iii) a tissue 3D model or a portion thereof, (iv) the 3D mesh or a portion thereof, (v) a marker indicating a specific location of interest within one or more of the aforementioned medical image, skin marker, skin 3D model, tissue 3D model, or 3D mesh, and/or the like.

Pre-Processing and Runtime Processing on Different Devices

In some implementations, one or more of the pre-processing operations described herein (e.g., processing of the medical images, generation of the 3D model, and/or generation of the skin marker) are performed on a device different from the device on which the runtime processing operations (e.g., 3D depth scanning, registration, and/or superimposing medical images over real-time camera view) are performed. In other implementations, all of the pre-processing operations and the runtime processing operations are performed on the same device (e.g., computing device 102).

Instructions Stored on Non-Transitory Computer-Readable Medium (CRM)

The techniques described herein may be implemented as a set of instructions stored on non-transitory computer-readable medium that, when executed by a computer (e.g., server computer, tablet computer, etc.), cause the computer to perform one or more of the operations described herein. The set of instructions may be packaged as an application or a set of software modules and downloaded onto the computer. The set of instructions can reside in RAM memory, flash memory, ROM memory, EPROM memory, EEPROM memory, registers, hard disk, a removable disk, a CD-ROM, or any other form of a non-transitory computer-readable storage medium.

Same Set of Instructions on Different CRMs

In some implementations, the same set of instructions are stored (e.g., as identical applications) on one CRM in communication with a first computer, and another CRM in communication with a second computer, where the set of instructions causes the first computer to perform the pre-processing steps described herein, and causes the second computer to perform the runtime processing steps described herein.

Different Sets of Instructions on Different CRMs

In some implementations, different sets of instructions are stored (e.g., as two different applications) on different CRMs of different computers, where one set of instructions stored on one CRM causes a first computer to perform the pre-processing steps described herein, and another set of instructions stored on another CRM causes a second computer to perform the runtime processing steps described herein.

Same Set of Instructions on Single CRM

In some implementations, one set of instructions are stored (e.g., as a single application) on a CRM of a computer, where the set of instructions causes the computer to perform the pre-processing steps described herein, and also causes the computer to perform the runtime processing steps described herein.

Different Sets of Instructions on Single CRM

In some implementations, different sets of instructions are stored (e.g., as two different applications) on a single CRM of a computer, where one set of instructions causes the computer to perform the pre-processing steps described herein, and another set of instructions causes the computer to perform the runtime processing steps described herein.

Alternative Timing of Skin Marker Generation

In some implementations, the skin marker is generated prior to runtime (e.g., before the patient is prepared for the medical procedure and before 3D depth scanning of the patient). In other implementations, the skin marker is generated at runtime (e.g., while the patient being prepared for the medical procedure or thereafter) but before 3D depth scanning of the patient. In other implementations, the skin marker is generated at runtime (e.g., while the patient being prepared for the medical procedure or thereafter) and after 3D depth scanning of the patient.

Flowchart for Pre-Processing Medical Images and Generating a Skin Marker

Figure 6:
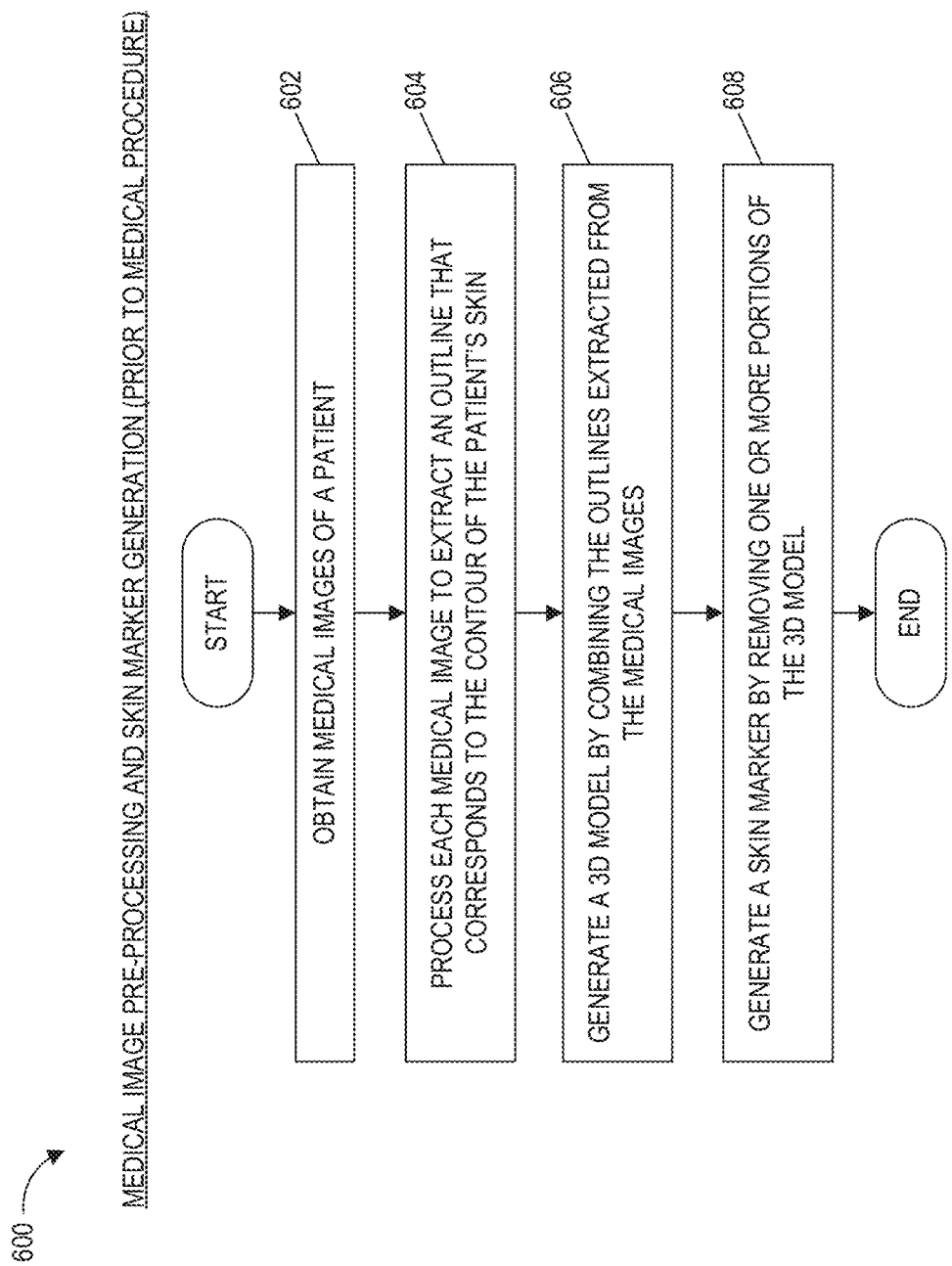
FIG. 6 illustrates a flowchart depicting a method for pre-processing medical images and generating a skin marker, according to an example implementation.

FIG. 6 is a flowchart depicting a method for pre-processing medical images and generating a skin marker, according to an example implementation. The steps illustrated in FIG. 6 may be performed, for example, by the computing device 102 operated by a medical professional performing a medical procedure on a patient, by another computing device different from that used to provide the real-time views at runtime, by a server computer in communication with the computing device 102, just to name a few examples. For convenience, the method 600 is described as performed by computing device 102.

Obtaining Medical Images

At block 602, the computing device 102 obtains medical images of a patient. For example, one or more medical images of the patient such as CT or MRI images may have been taken to visualize the inside of the patient's body and provide an appropriate diagnosis. Such images can be transferred onto the computing device 102 for pre-processing before runtime.

Pre-Processing Medical Images

At block 604, the computing device 102 processes each medical image to extract an outline (e.g., a collection of vertices or pixels/voxels) that corresponds to the contour of the patient's skin. For example, the segmentation process described herein may be used to extract the outline.

Generating 3D Model

At block 606, the computing device 102 generates a 3D model by combining the outlines extracted from the medical images. For example, the meshing process described herein may be used to generate the 3D model.

Generating Skin Marker

At block 608, the computing device 102 generates a skin marker by removing one or more portions of the 3D model. For example, the skin marker may be generated based on the target portions and/or the noise portions, as described herein.

Flowchart for Processing Patient Image and Superimposing Medical Images

Figure 7:
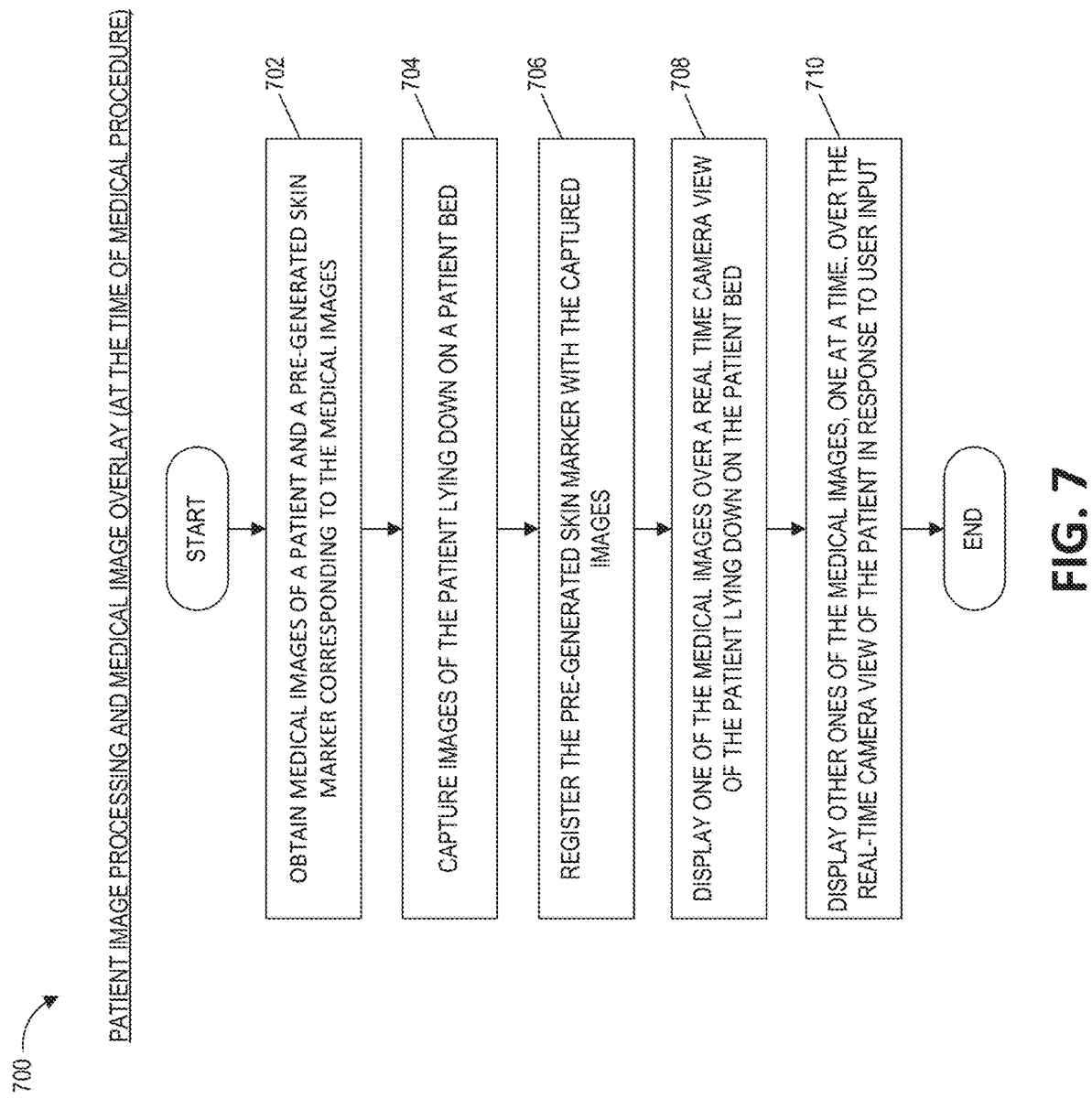
FIG. 7 illustrates a flowchart depicting a method for processing a patient's images and superimposing the medical images over the real-time camera view, according to an example implementation.

FIG. 7 is a flowchart depicting a method for processing a patient's images and superimposing the medical images over the real-time camera view, according to an example implementation. The steps illustrated in FIG. 7 may be performed, for example, by the computing device 102 operated by a medical professional performing a medical procedure on a patient. For convenience, the method 700 is described as performed by computing device 102.

Obtaining Medical Images and Pre-Generated Skin Marker

At block 702, the computing device 102 obtains medical images of a patient and a pre-generated skin marker corresponding to the medical images.

Capturing Patient Images

At block 704, the computing device 102 captures 3D images of the patient lying down on a surgical bed. For example, the computing device 102 may use a 3D depth camera connected thereto to capture the 3D images, as described herein.

Registering Pre-Generated Skin Marker to Captured Patient Images

At block 706, the computing device 102 registers the pre-generated skin marker to the captured 3D images. For example, the features in the skin marker may be aligned to the features in the 3D images (or a 3D model generated based on the 3D images), and the coordinate system of the skin marker may be registered to the coordinate system of the computing device 102 based on the alignment.

Displaying Medical Image over Real-Time Camera View

At block 708, the computing device 102 displays, on a display device, one of the medical images over a real-time camera view of the patient lying on the surgical bed.

Scrolling Through Other Medical Images

At block 710, the computing device 102 displays other ones of the medical images, one at a time, over the real-time camera view of the patient in response to user input.

Example Architecture of User Computing System

Figure 8:
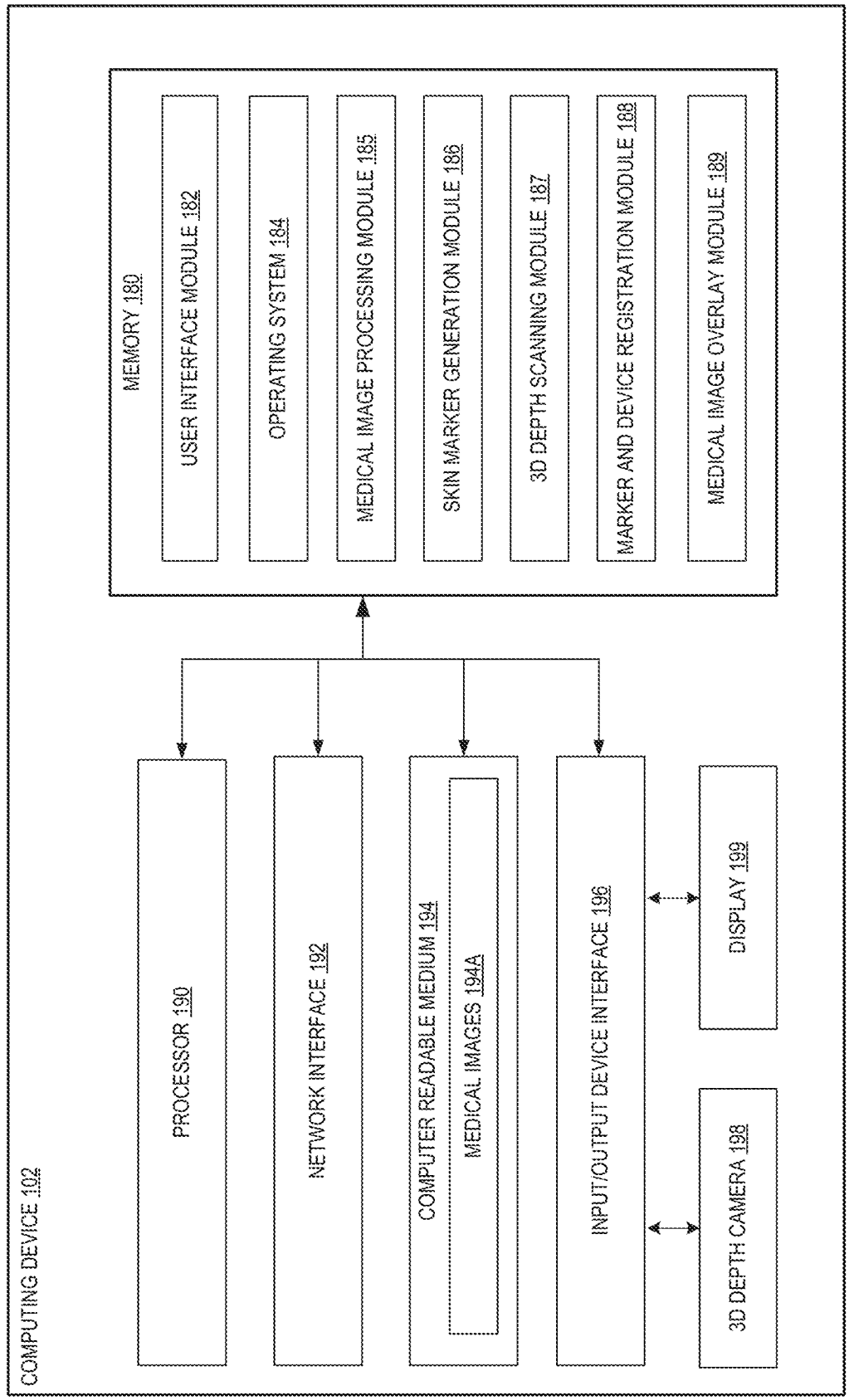
FIG. 8 illustrates an implementation of a computing device, according to an example implementation.

FIG. 8 depicts an example architecture of a computing device 102 that can be used to perform one or more of the techniques described herein or illustrated in FIGS. 1-7. The general architecture of the computing device 102 depicted in FIG. 8 includes an arrangement of computer hardware and software modules that may be used to implement one or more aspects of the present disclosure. The computing device 102 may include many more (or fewer) elements than those shown in FIG. 8. It is not necessary, however, that all of these elements be shown in order to provide an enabling disclosure. As illustrated, the computing device 102 includes a processor 190, a network interface 192, a computer readable medium 194, and an input/output device interface 196, all of which may communicate with one another by way of a communication bus. The network interface 192 may provide connectivity to one or more networks or computing systems. The processing 190 may also communicate with memory 180 and further provide output information for one or more output devices, such as a display (e.g., display 199), speaker, etc., via the input/output device interface 196. The input/output device interface 196 may also accept input from one or more input devices, such as a camera (e.g., 3D depth camera 198), keyboard, mouse, digital pen, microphone, touch screen, gesture recognition system, voice recognition system, accelerometer, gyroscope, etc.

The memory 180 may contain computer program instructions (grouped as modules in some implementations) that the processor 190 executes in order to implement one or more aspects of the present disclosure. The memory 180 may include RAM, ROM, and/or other persistent, auxiliary, or non-transitory computer-readable media. The memory 180 may store an operating system 184 that provides computer program instructions for use by the processor 190 in the general administration and operation of the computing device 102. The memory 180 may further include computer program instructions and other information for implementing one or more aspects of the present disclosure. For example, in one implementation, the memory 180 includes a user interface module 182 that generates user interfaces (and/or instructions therefor) for display, for example, via a browser or application installed on the computing device 102.

In addition to and/or in combination with the user interface module 182, the memory 180 may include a medical image processing module 185, a skin marker generation module 186, a 3D depth scanning module 187, a marker and device registration module 188, and a medical image overlay module 189 that may be executed by the processor 190. In one implementation, the medical image processing module 185 processes the medical images of a patient to generate a 3D model of the patient, the skin marker generation module 186 removes portions of the generated 3D model to generate a skin marker, the 3D depth scanning module 187 causes the 3D depth camera 198 to capture 3D images of the patient, the marker and device registration module 188 uses the skin marker to register the coordinate system of the 3D model and the medical images with the coordinate system of the computing device 102, and the medical image overlay module 189 causes the medical images to be superimposed over the real-time camera view of the 3D depth camera 198 (or another camera on the computing device 102) displayed via the display 199 of the computing device 102. The operations and algorithms of the modules 185-189 are described in greater detail above with reference to FIGS. 1-7.

Although a single processor, a single network interface, a single computer readable medium, a singer input/output device interface, a single memory, a single 3D depth camera, and a single display are illustrated in the example of FIG. 8, in other implementations, the computing device 102 can have a multiple of one or more of these components (e.g., two or more processors and/or two or more memories).

Other Considerations

Logical blocks, modules or units described in connection with implementations disclosed herein can be implemented or performed by a computing device having at least one processor, at least one memory and at least one communication interface. The elements of a method, process, or algorithm described in connection with implementations disclosed herein can be embodied directly in hardware, in a software module executed by at least one processor, or in a combination of the two. Computer-executable instructions for implementing a method, process, or algorithm described in connection with implementations disclosed herein can be stored in a non-transitory computer readable storage medium.

Although the implementations of the inventions have been disclosed in the context of certain implementations and examples, it will be understood by those skilled in the art that the present inventions extend beyond the specifically disclosed implementations to other alternative implementations and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the implementations may be made and still fall within one or more of the inventions. Accordingly, it should be understood that various features and aspects of the disclosed implementations can be combined with or substituted for one another in order to form varying modes of the disclosed inventions. Thus, it is intended that the scope of the present inventions herein disclosed should not be limited by the particular disclosed implementations described above, and that various changes in form and details may be made without departing from the spirit and scope of the present disclosure as set forth in the following claims.

What is claimed is:

1. A method comprising:
   processing medical image data comprising a plurality of 2D cross-sectional images of a patient's body to generate a skin 3D model that represents a 3D contour of the patient's skin;
   processing the skin 3D model to generate a skin marker for use in a proposed medical procedure to treat or examine a target tissue of the patient, wherein processing of the skin 3D model comprises removing, from the skin 3D model, one or both of:
   (1) a first portion of the skin 3D model corresponding to a first skin area of the patient that would contact or directly face a supporting surface on which the patient would lie during the proposed medical procedure, and
   (2) a second portion of the skin 3D model corresponding to a second skin area of the patient adjacent to a shoulder joint of the patient's body that would substantially change its position relative to the target tissue and/or substantially change its contour as an arm linked to the shoulder joint moves about the shoulder joint, such that the skin marker comprises at least part of the skin 3D model excluding one or both of the first portion and the second portion therefrom;

subsequent to generating the skin marker, capturing images of the patient who is lying on a patient bed for the medical procedure; and processing the captured images of the patient and the skin marker to register them for augmented reality without use of an artificial physical marker fixed to or placed on the patient's body.

2. The method of claim 1, wherein processing the skin 3D model comprises removing both the first portion and the second portion such that the skin marker comprises at least part of the skin 3D model excluding therefrom both the first portion and the second portion.

3. The method of claim 1, wherein the patient's body comprises a target body part encompassing the target tissue and a non-target body part that is connected to the target body part via a joint, wherein the skin 3D model comprises a 3D contour of the patient's skin of the target body part and a 3D contour of the patient's skin of the non-target body part, wherein processing the skin 3D model comprises further removing the 3D contour of the patient's skin of the non-target body part.

4. The method of claim 1, wherein the method further comprises rendering a real-time augmented reality view, in which at least one of the plurality of 2D cross-sectional images showing the target tissue is superimposed on one or more additional real-time images captured subsequent to registration of the captured images of the patient and the skin marker.

5. The method of claim 4, further comprising, prior to the medical procedure, processing the medical image data to generate a tissue 3D model for use in the medical procedure, wherein the tissue 3D model defines a 3D contour enclosing at least part of the target tissue and is located inside the skin 3D model, wherein the real-time augmented reality view further comprises the tissue 3D model superimposed on one or more additional captured images of the patient.

6. The method of claim 1, wherein processing the skin 3D model comprises further removing a portion of the skin 3D model corresponding to the patient's skin area that would be covered with a medical drape and therefore would not be exposed during the medical procedure.

7. The method of claim 1, wherein processing the skin 3D model comprises further removing a portion of the skin 3D model corresponding to the patient's abdomen that would substantially change its contour before and after the patient's meal.

8. The method of claim 1, wherein the skin marker comprises at least two portions corresponding to the patient's skin areas that are not connected to each other.

9. The method of claim 1, further comprising placing a medical drape over the patient lying on the patient bed in a manner that leaves a skin portion of the patient's body exposed, wherein the placing of the medical drape is performed before or after capturing the images of the patient.

10. The method of claim 1, further comprising placing a medical drape over the patient lying on the patient bed while leaving a skin area exposed, wherein the placing of the medical drape is performed after capturing of the images of the patient, wherein the skin marker does not comprise a portion of the skin 3D model corresponding to the skin area that is left exposed.

11. The method of claim 1, wherein the skin marker does not comprise a portion of the skin 3D model corresponding to the patient's skin area that is closest to the target tissue.

12. The method of claim 1, wherein processing the skin 3D model comprises further removing at least one portion of the skin 3D model corresponding to at least one skin area of the patient's body potions selected from the group consisting of abdomen, armpit, and limb.

13. The method of claim 1, wherein processing the skin 3D model comprises further removing at least one portion of the skin 3D model corresponding to at least one skin area of the patient's body potions selected from the group consisting of pubic region, densely populated hair region, and mouth.

14. The method of claim 1, wherein processing the skin 3D model comprises keeping a portion thereof corresponding to the patient's cheekbone or ear.

15. A non-transitory storage medium storing a plurality of instructions executable by a computer, wherein the plurality of instructions, when executed, causes the computer:

to receive medical image data comprising a plurality of 2D cross-sectional images of a patient's body that encompasses a target tissue;

to process the medical image data to generate a skin 3D model defining a 3D contour of the patient's skin;

to receive information about the target tissue and information about a proposed medical procedure to treat or examine the target tissue; and to remove, from the skin 3D model, one or both of:
(1) a first portion of the skin 3D model corresponding to a first skin area of the patient that would contact or directly face a lying surface on which the patient would lie during the proposed medical procedure, and
(2) a second portion of the skin 3D model corresponding to a second skin area of the patient adjacent to a shoulder joint of the patient's body that would substantially change its position relative to the target tissue and/or substantially change its contour as an arm linked to the shoulder joint moves about the shoulder joint, thereby providing a skin marker that comprises at least part of the skin 3D model excluding one or both of the first portion and the second portion therefrom.

16. The non-transitory storage medium of claim 15, wherein the plurality of instructions, when executed, further causes the computer:

to capture images of the patient;

to process the captured images of the patient and the skin marker to register them for augmented reality without use of an artificial physical marker fixed to the patient's body or worn by the patient; and to render a real-time augmented reality view comprising at least one of the plurality of 2D cross-sectional images of the patient's body superimposed on one or more additional images of the patient captured subsequent to registration of the captured images of the patient and the skin marker.

17. The non-transitory storage medium of claim 16, wherein the computer is a handheld computing device, wherein the plurality of instructions, when executed, further causes the handheld computing device to render, on the handheld computing device, one or both of (a) a mesh of the skin 3D model and (b) a mesh of the skin marker.

18. The non-transitory storage medium of claim 15, wherein the skin marker comprises at least two portions corresponding to the patient's skin areas that are not connected to each other.

19. The non-transitory storage medium of claim 15, wherein both the first portion and the second portion are removed from the skin 3D model to provide the skin marker comprises at least part of the skin 3D model excluding both the first portion and the second portion therefrom.

20. The non-transitory storage medium of claim 15, wherein the patient's body comprises a target body part encompassing the target tissue and a non-target body part that is connected to the target body part via a joint, wherein the skin 3D model comprises a 3D contour of the patient's skin of the target body part and a 3D contour of the patient's skin of the non-target body part, wherein the plurality of instructions, when executed, causes the computer to further remove the 3D contour of the patient's skin of the non-target body part.

* * * * *